United States Patent [19]

Khan et al.

[11] Patent Number: 5,180,061

[45] Date of Patent: Jan. 19, 1993

[54] STABLE IODOPHOR IN POLYURETHANE FOAM

[75] Inventors: Mohammad A. Khan, Sandy; Minh Q. Hoang, Taylorsville, both of Utah

[73] Assignee: Becton, Dickinson and Company, Franklin Lakes, N.J.

[21] Appl. No.: 756,661

[22] Filed: Sep. 9, 1991

[51] Int. Cl.$^5$ ............................................. A61B 19/02
[52] U.S. Cl. .................................. 206/570; 206/229; 206/438; 206/440; 424/667; 15/104.94
[58] Field of Search ............... 206/570, 229, 438, 440, 206/370; 15/104.93, 104.94; 424/667, 669, 405, 402, 411; 514/941

[56] References Cited

U.S. PATENT DOCUMENTS

| | | |
|---|---|---|
| 3,235,446 | 2/1966 | Shelanski et al. . |
| 3,619,843 | 11/1971 | Richter et al. ................... 15/104.93 |
| 4,017,407 | 4/1977 | Cantor et al. . |
| 4,113,857 | 9/1978 | Shetty . |
| 4,271,149 | 6/1981 | Winicov et al. . |
| 4,323,656 | 4/1982 | Strickman et al. .......... 15/104.93 X |
| 4,355,021 | 10/1982 | Mahl et al. ....................... 424/667 X |
| 4,381,380 | 4/1983 | LeVeen et al. . |
| 4,597,975 | 7/1986 | Woodward et al. . |
| 4,847,089 | 7/1989 | Kramer et al. .............. 15/104.93 X |
| 4,856,541 | 8/1989 | Kellett et al. ................ 15/104.94 X |
| 4,873,354 | 10/1989 | Globus . |
| 4,893,956 | 1/1990 | Wojcik et al. ............... 15/104.94 X |
| 5,000,749 | 3/1991 | LeVeen et al. . |
| 5,020,182 | 6/1991 | Engel ............................ 15/104.94 X |

Primary Examiner—Jimmy G. Foster
Assistant Examiner—Jacob K. Ackun, Jr.
Attorney, Agent, or Firm—Richard E. Brown; Nanette S. Thomas

[57] ABSTRACT

A surgical scrub includes a polyurethane foam sponge impregnated with a composition which includes iodine, iodide and a nonionic surfactant in a polar vehicle. The scrub may be attached to a plastic handle and may be supplied along with other optional scrubbing items in a package wrapped in plastic film.

6 Claims, No Drawings

STABLE IODOPHOR IN POLYURETHANE FOAM

BACKGROUND OF THE INVENTION

1. Field of the Invention

This invention relates to an iodophor and more particularly relates to a polyurethane sponge containing the iodophor and release of iodine therefrom.

2. Background

Iodine is a well-known germicide with activity against a wide range of bacteria and viruses, and much effort has been directed to finding satisfactory vehicles for its administration. Compounds which form complexes with iodine, such a polyvinylpyrrolidone (PVP) and surfactants have been used. The term iodophor is a conventional designation for these iodine-containing complexes.

Polyurethane foams are disclosed as iodophors by Shelanski et al. in U.S. Pat. No. 3,235,446. In the Shelanski et al. invention, a surfactant having hydroxyl end groups reacts with a diisocyanate and becomes part of the polyurethane chain. The Shelanski polyurethane foam complexes iodine, and, when dry releases into water considerably less iodine than originally complexed.

A polyurethane foam which complexes iodine and PVP is disclosed by LeVeen et al. in U.S. Pat. No. 4,381,380. LeVeen et al. reports that the complexed iodine is slowly dissociable from the foam.

Cantor et al., in U.S. Pat. No. 4,017,407 discloses a solid PVP iodophor containing a compatible anionic or nonionic surfactant Globus, in U.S. Pat. No. 4,873,354, discloses a stable complex of iodine with a polyethylene glycol ester of an alkylarylsulfonic acid. In the Globus disclosure, iodine serves a dual role as a germicide in the iodophor and as a catalyst for the esterification. About one half of the iodine used is available as the germicide.

Iodophors impregnated into a sponge are often mated with a scrub and used for germicidal cleansing or scrubbing. Often, such implements are included in a kit of materials which may also include other items useful for patient preparation, such as towels, gloves and the like. Problems often arise in use of iodine as a germicide. A typical iodophor product is provided and used in the presence of water. Iodine and water undergo a well known but complex series of reactions leading, among other species, to iodide ions and hydrogen ions. The production of hydrogen ions may reduce the pH of a topical iodine preparation enough to cause skin irritation and discomfort to the user. Loss of iodine titer causes an additional problem of assuring that the iodine content of a composition does not fall below the stated concentration on the label during its time on the shelf.

Another problem arises when the iodophor is used with a polyurethane foam sponge. Iodine complexes strongly with polyurethane, and any iodine which is not released from the polyurethane complex is not available as germicide.

Accordingly, a variety of approaches has focused on ways to stabilize the iodine concentration in an iodophor-iodine complex. U.S. Pat. No. 4,271,149 to Winicov et al. discloses a germicidal iodine composition of stabilized iodine concentration. The composition contains an organic material, iodine, iodide ion and iodate ion and is maintained at a pH of from 5 to 7 wherein the iodide and iodate react in the presence of hydrogen ions to replenish iodine lost during storage.

U.S. Pat. No. 4,113,857 to Shetty discloses a method to stabilize a preformed iodophor-iodine complex by adding an oxidizing agent, such as iodate ion, and to prepare a complex by reacting an iodophor, such as providone, with iodate and iodide ions.

An iodine surfactant germicidal cleansing composition is disclosed in U.S. Pat. No. 4,597,975 to Woodward et al. In the Woodward et al. composition, low concentrations of iodine are stabilized as the triiodide salt by complexing with an amine oxide surfactant. When solubilized by excess amine oxide, the triiodide salt has a very low iodine vapor pressure and high germicidal activity.

LeVeen et al. in U.S. Pat. No. 5,000,749 discloses a contraceptive sponge containing iodine in which the iodine is complexed to the polyurethane and is slowly liberated over many days.

Although the above disclosures have improved iodine and iodophor stability, there remains a need for further improvement, particularly when the iodine is used with a polyurethane during a prolonged shelf time. It is toward fulfillment of this need that the present invention is directed.

SUMMARY OF THE INVENTION

A surgical scrub includes a polyurethane foam sponge impregnated with a germicidal composition which includes iodine, iodide and a nonionic surfactant in a polar vehicle. The sponge preferably is affixed to a plastic handle and may be packaged in a plastic film wrap along with other items useful for scrubbing such as a nail pick, a wipe, a bristle and the like.

Preferred nonionic surfactants are the octyl-phenoxypolyoxyethylenealcohols and the polyoxyethylenepolyoxypropylene polyols.

The polar vehicle may preferably be an alkylene glycol, preferably propylene glycol. The glycol may contain water. The most preferred vehicle is propylene glyco which is essentially water free.

When water is absent, the nonionic surfactant is present in at least 12% by weight of the composition (in the present disclosure, all percentages are by weight). When water is present, at least 21% of the surfactant is present in the composition. With these percentages of nonionic surfactant in the composition, the iodine complexes strongly to the surfactant so that little complexation to the polyurethane takes place.

Thus, the invention provides a sponge for surgical scrubbing which includes iodine in a form which facilitates substantially instantaneous release of most of the iodine when the scrub is contacted with water. Because of the rapid release and instantaneous availability of the iodine, an aqueous solution brought into contact with the scrub reaches an antimicrobially effective level of germicide suitable for scrubbing immediately on contact with water. The advantage to a surgeon of not having to wait for release of iodine before starting to scrub is immediately evident.

The iodine complexed to a bolus of a nonionic surfactant does not react with water and, therefore, provides a further advantage in overcoming the well-known loss of iodine titer of prior art iodine preparations so that the iodine titer of the present composition remains substantially unchanged during storage.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments described. The scope of the invention will be measured by the appended claims and their equivalents.

In accordance with the present invention, iodine may be complexed with at least 12% of the nonionic surfactant in a polar vehicle to give a composition which can be impregnated in a polyurethane sponge with substantially less complexation between the iodine and the polyurethane than occurs when an ionic (anionic or cationic) surfactant is used. Accordingly, the composition of the present invention comprises iodine, iodide, a nonionic surfactant and a polar vehicle and is substantially free of ionic surfactant.

The polar vehicle may be alcohol, a glycol, a liquid polyglycol or mixtures thereof. The polar vehicle may contain water. Preferred vehicles are liquid polyethyleneglycols (CARBOWAX ®, Union Carbide Corp.), liquid alkyl ethers of polyethylene glycol (PLURACOL ®, BASF Corp.) and mixtures thereof. The most preferred polar vehicle is propyleneglycol, alone or mixed with the water. In mixtures of water and the polar vehicle, the water content may be from 1 to about 77%, preferably 5 to 50%.

Iodine may be present in the composition in about 0.1 to 3.0%, preferably about 0.5 to 1.5%, most preferably about 1.0%. Similarly, iodide, in the form of sodium or potassium iodide, may be present in the composition in about 0.1 to 2.0, preferably about 0.5 to 1.0, most preferably about 0.5%.

A nonlimiting list of suitable nonionic surfactants includes polyoxyethylene sorbitan esters and ethers, and preferably the PLURONIC ® series of polyoxyethylenepolyoxypropylene polyols available from BASF Corp. and the IGEPAL ® series of alkylphenoxypolyoxyethylene alcohols available from GAF Corp. A single nonionic surfactant or a mixture may be used. For those compositions which do not contain water, the nonionic surfactant may be present in about 12 to 25%. For those compositions which do contain water, about 21 to 50% of nonionic surfactant is contemplated.

Other conventional ingredients may be added to the composition if desired. For example, the composition may include thickening agents, emollients, and a fragrance compound added to give the composition a pleasing scent.

The germicidal composition of the invention may be used in conjunction with a polyurethane foam sponge in a surgical scrub. The sponge may be synthesized from a polyisocyanate, a polyglycol, a chain extender and a blowing agent. Polyurethane foam sponges are wholly conventional in the art and no further details on this feature of the invention are needed for a full understanding of the invention. The polyglycol may be a polyester glycol or preferably a polyether glycol. Thus, preferred polyurethanes are polyetherurethanes.

When the composition and the sponge are brought into contact, the composition is taken up into the sponge to give the scrub of the invention. It has been found that, when the composition includes at least 12% of the nonionic surfactant and is substantially free of water, minimal complexing between the iodine and the polyurethane takes place. If the composition includes water, the nonionic surfactant is preferably present in at least 21% to minimize complexing between the iodine and the polyurethane.

When the scrub is squeezed into water in preparation for use, a high percentage of the iodine, because it is not complexed with the polyurethane, passes quickly into the water to act as a germicidal agent, and little iodine is lost due to iodine-polyurethane complexation.

In contrast, a composition containing a lower percentage of nonionic surfactant or an anionic or cationic surfactant has significantly weaker complexation between the iodine and the surfactant. When such a composition is taken up into the sponge, this weaker complexation is overcome by a stronger complexation of the iodine with the polyurethane so that when the scrub is squeezed into water, less iodine is released into the water.

The extent of complexation between the iodine and the polyurethane may be determined by measuring the percent of available iodine, determined by thiosulfate titration as given in Example III, after water washing of the sponge. In addition, a visual indication of iodine polyurethane complexation is given by the color of the sponge after washing, as described in Example V. In this experiment, a darker color means more complexation.

Table I below lists representative compositions of the invention. Table II shows, for comparison purposes, compositions outside of the invention. All components of the compositions in the Tables are given in percent by weight and contain the preferred 1.0% iodine and 0.5% potassium iodide.

TABLE I

| Composition | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|
| PLURONIC ® L-84 | 10 | | | | | | | 10 | 10 | | 10 | | | | | | |
| PLURONIC ® L-31 | 5 | | | | | | | 5 | 5 | | 5 | | | | | | |
| PLURONIC ® L-64 | | 10 | | | | 10 | 10 | | | 10 | | 20 | 20 | 10 | 10 | 20 | 20 |
| PLURONIC ® L-35 | | 5 | | | | 5 | 5 | | | 5 | | 10 | 10 | 5 | 5 | 10 | 10 |
| IGEPAL ® CA-630 | 6 | 6 | 21.0 | 16.0 | 12.0 | 6 | 6 | 6 | 6 | | | 6 | 8 | 6 | 6 | | |
| PROPYLENE GLYCOL | 77.5 | 77.5 | 77.5 | 82.5 | 86.5 | | | | | 83.5 | 83.5 | | | | | | |
| CARBOWAX ® 400 | | | | | | 77.5 | | 77.5 | | | | | | 27.5 | | 18.5 | |
| PLURACOL ® W-170 | | | | | | | 77.5 | | 77.5 | | | | | | 27.5 | | 18.5 |
| WATER | | | | | | | | | | | | 62.5 | 45.0 | 50 | 50 | 50 | 50 |
| AVAILABLE I₂ 4 weeks | 0.78 | 0.77 | 0.80 | 0.80 | 0.73 | | | | | 0.77 | | 0.77 | | | | | |
| STAIN* | 0 | 0 | 0 | 0 | 0-1 | 0 | 0 | 0 | 0 | 0-1 | 0 | 0 | 0 | 0 | 0 | 0 | 0 |

*Stain graded as given in Example V

TABLE II

| Composition | 18 | 19 | 20 | 21 | 22 | 23 | 24 | 25 | 26 | 27 | 28 | 29 | 30 |
|---|---|---|---|---|---|---|---|---|---|---|---|---|---|
| PLURONIC ® L-84 |  |  |  | 10 |  |  |  | 5 | 7 | 8 | 5 | 8 |  |
| PLURONIC ® L-31 |  |  |  | 5 |  |  |  |  |  |  | 2.5 | 4 |  |
| PLURONIC ® L-64 |  |  |  |  | 10 | 10 | 20 |  |  |  |  |  |  |
| PLURONIC ® L-35 |  |  |  |  | 5 | 5 | 10 | 2.5 | 3 | 4 |  |  |  |
| IGEPAL ® CA-630 | 6 | 6 | 6 | 6 | 6 | 6 |  |  |  |  |  |  | 6 |
| IGEPAL ® CA-436 |  |  | 10 |  |  |  |  |  |  |  |  |  |  |
| ALIPAL ® HF-433** | 15 |  |  |  |  |  |  |  |  |  |  |  |  |
| MONAQUAT P-TC*** |  | 15 |  |  |  |  |  |  |  |  |  |  |  |
| PROPYLENE GLYCOL | 77.5 | 77.5 | 77.5 |  |  | 27.5 |  | 91 | 88.5 | 86.5 | 91.5 | 86.5 | 92.5 |
| WATER |  |  | 5 | 77.5 | 77.5 | 50 | 68.5 |  |  |  |  |  |  |
| AVAILABLE I$_2$ 4 weeks | .66 | .53 | .54 | .68 | .73 | .75 | .53 |  |  |  |  |  | .69 |
| STAIN* | 3 | 3 | 3 | 3 | 3 | 3 | 2 | 3 | 2 | 3 | 3 | 3 | 3 |

**Anionic surfactant (ammonium salt of sulfated nonylphenoxypoly(ethyleneoxy)ethanol)
***Cationic surfactant (fatty acid amido ammonium phosphate. Mona Industries, Inc., Paterson, New Jersey)

From Table I, it can be seen that water free compositions 1 to 11 having at least 12% of nonionic surfactant after 4 weeks shelf time in the polyurethane sponge, released about 73% or more of the iodine into a water wash and left the sponge substantially unstained. In contrast, Table II shows water-free compositions 18 and 19 having ionic surfactant and 25 to 30 having a low concentration of nonionic surfactant to release a substantially lower percentage of available iodine and leave the sponge stained with complexed iodine.

Compositions 12 to 17 which include water require higher percentages of nonionic surfactant to complex the iodine sufficiently to release 75% of the iodine and leave the sponge unstained after 4 weeks shelf time, and may be compared with compositions 20 to 24 which give lower percentages of iodine recovery and/or stained sponge after washing.

The sponge may of course be used for germicidal cleansing by itself, but preferably is used in conjunction with a handle in a scrub unit. In this embodiment of the invention, the sponge may be conventionally affixed to a plastic, preferably polyethylene handle. The handle may also carry bristles as an aid in scrubbing. The sponge loaded with the germicidal composition, or preferably the scrub unit, may be included in a plastic package for surgical scrubbing. The package may also include other components, such as a nail cleaner and paper or cloth wipes as further aids in surgical scrubbing.

The following examples are provided to further illustrate the invention but are not to be considered as limitative in any way.

EXAMPLE I

Procedures for Preparing Composition

The polar vehicle was placed in a suitable sized vessel equipped with stirrer. The iodine was added with stirring to prevent clumping. The nonionic surfactant was added slowly with stirring to avoid excessive foaming, followed by the sodium iodide. The mixture was stirred for about 30 min until the composition was homogeneous.

EXAMPLE II

Preparation of Scrub/Sponge Unit

A scrub unit having a polyethylene handle attached to a polyurethane foam sponge was placed in a preformed boat type of packaging unit. the germicidal composition (33 ml) was injected into the sponge and allowed to spread uniformly throughout the sponge. A nail pick was placed on top of the sponge. A polymeric film lidding was placed over the boat and heat sealed.

EXAMPLE III

Determination of Available Iodine

The unopened sample package was weighed. The contents were added to a clean 1,000 ml beaker, and the inside of the package was rinsed with water which was added to the beaker. Water was added to the beaker up to about 200 ml. Wil stirring, titration with standardized sodium thiosulfate was performed until the solution turned clear. Two more titrations after 10 minute intervals were performed to allow for additional iodine release from the sponge. All parts of the original sample package were recombined and dried for 24 hours to constant weight.

Calculation $$\% \text{ available iodine} = \frac{\text{volume Na}_2\text{S}_2\text{O}_3 \times \text{normality} \times 12.69}{\text{weight loss}}$$

EXAMPLE IV

Comparative Example

Solutions of iodine (2q, 4q) were prepared in 100 g each of nonylphenoxypolyoxyethylene alcohol. These solutions were applied to a polyurethane foam sponge as described in Example II. The sponges were washed with water until the color was constant. The color of the sponge after washing was observed to be dark brown, indicating a level 3 complexation of the iodine and polyurethane, as described in Example V.

EXAMPLE V

Visual Evaluation of Complexation

The surgical hand scrub package was opened and the sponge loaded with the composition of the invention, dark brown in color, was washed with water until the color was constant. The color was judged as follows:

0—color of sponge without composition
1—tan
2—medium brown
3—dark brown

Iodine complexed with the polyurethane does not with water so that the sponge remains brown. If the iodine is complexed strongly with the nonionic surfactant, it does not complex with the polyurethane and is washed out with water. Thus, this experiment is a subjective evaluation of the extent to which the nonionic detergent prevents the detrimental complexation of the iodine with polyurethane which renders the iodine unavailable for germicidal use.

What is claimed is:

1. A surgical scrub comprising a polyurethane sponge and a germicidal composition impregnated in said sponge, said composition comprising iodine, iodide, a polar vehicle and at least 12% of a nonionic surfactant when the composition if essentially water free and at least 21% of said nonionic surfactant when the composition includes water.

2. The scrub of claim 1 wherein the percentage of said iodine in the composition is about 0.5 to 1.5%.

3. The scrub of claim 1 wherein the percentage of said iodide is about 0.5 to 1.0%.

4. The scrub of claim 1 wherein said nonionic surfactant is selected from the group consisting of a polyoxyethylene sorbitan, polyoxyethylene-polyoxypropylene polyol and an alkylphenoxypolyoxyethylene alcohol.

5. The scrub of claim 1 wherein said polar vehicle is selected from the group consisting of an alcohol, a glycol, a liquid polyalkyleneglycol, a liquid alkyl ether or ester of a polyalkyleneglycol, a mixture thereof and a mixture thereof containing water.

6. The scrub of claim 1 further comprising a molded polymeric handle having said sponge attached thereto.

* * * * *